(12) United States Patent
Li et al.

(10) Patent No.: US 11,112,527 B2
(45) Date of Patent: Sep. 7, 2021

(54) METHOD AND SYSTEM FOR DETERMINING HETEROGENEOUS CARBONATE RESERVOIR SATURATION EXPONENT

(71) Applicant: PetroChina Company Limited, Beijing (CN)

(72) Inventors: Ning Li, Beijing (CN); Kewen Wang, Beijing (CN); Yujiang Shi, Beijing (CN); Hongliang Wu, Beijing (CN); Taiping Zhao, Beijing (CN); Qingfu Feng, Beijing (CN); Zhou Feng, Beijing (CN); Haitao Zhang, Beijing (CN); Baoding Zhu, Beijing (CN); Xiaoming Yang, Beijing (CN)

(73) Assignee: PetroChina Company Limited, Beijing (CN)

( * ) Notice: Subject to any disclaimer, the term of this patent is extended or adjusted under 35 U.S.C. 154(b) by 442 days.

(21) Appl. No.: 16/095,432

(22) PCT Filed: May 15, 2017

(86) PCT No.: PCT/CN2017/084304
§ 371 (c)(1),
(2) Date: Oct. 22, 2018

(87) PCT Pub. No.: WO2018/028258
PCT Pub. Date: Feb. 15, 2018

(65) Prior Publication Data
US 2019/0137648 A1    May 9, 2019

(30) Foreign Application Priority Data
Aug. 10, 2016 (CN) .......................... 201610649337.4

(51) Int. Cl.
*G01V 3/38* (2006.01)
*G01N 33/24* (2006.01)
(Continued)

(52) U.S. Cl.
CPC ................ *G01V 3/38* (2013.01); *E21B 49/00* (2013.01); *G01N 33/24* (2013.01); *G01V 3/18* (2013.01); *G01V 99/005* (2013.01)

(58) Field of Classification Search
CPC .......... G01V 3/38; G01V 99/005; G01V 3/18; G01N 33/24; E21B 49/00
See application file for complete search history.

(56) References Cited

U.S. PATENT DOCUMENTS 4,790,180 A * 12/1988 Sinnokrot ............... E21B 49/00
73/152.07
2004/0225441 A1* 11/2004 Tilke ........................ G01V 3/20
702/6
(Continued)

FOREIGN PATENT DOCUMENTS

CN    101806215 A    8/2010
CN    102175832 A    9/2011
(Continued)

OTHER PUBLICATIONS

Zhijiang Kang et al., "A Triple-Continuum Numerical Model for Simulating Multiphase Flow in Vuggy Fractured Reservoirs", XVI International Conference on Computational Methods in Water Resources (CMWRXVI), Ingeniørhuset (Kalvebod Brygge 31-33, 1780 Copenhagen V, Denmark), Jun. 18, 2006-Jun. 22, 2006 (Session General, P.*
(Continued)

*Primary Examiner* — Alexander Satanovsky
(74) *Attorney, Agent, or Firm* — Michael Best and Friedrich LLP

(57) ABSTRACT

The present application provides a method and a system for determining a saturation exponent of a heterogeneous car-
(Continued)

bonate reservoir. The method comprises: dividing a target reservoir into at least two reservoir types in accordance with a predetermined rule; obtaining a correspondence relationship between a saturation exponent and a bound water saturation in each of the reservoir types; determining the reservoir type to which a to-be-measured core belongs in accordance with the predetermined rule; obtaining a bound water saturation of the to-be-measured core; and calculating the saturation exponent of the to-be-measured core according to the bound water saturation of the to-be-measured core on the basis of the correspondence relationship of the reservoir type to which the to-be-measured core belongs.

8 Claims, 2 Drawing Sheets

(51) Int. Cl.
  G01V 99/00 (2009.01)
  E21B 49/00 (2006.01)
  G01V 3/18 (2006.01)

(56) References Cited

U.S. PATENT DOCUMENTS

| | | |
|---|---|---|
| 2005/0030019 A1 | 2/2005 | Fleury |
| 2012/0152548 A1* | 6/2012 | Hinkel ................ G01N 33/24 166/305.1 |
| 2013/0103319 A1* | 4/2013 | Buiting ................ G01V 11/00 702/12 |
| 2015/0212227 A1* | 7/2015 | Chen .................... G01V 3/34 324/303 |

FOREIGN PATENT DOCUMENTS

| | | |
|---|---|---|
| CN | 102243196 A | 11/2011 |
| CN | 102434152 A | 5/2012 |
| CN | 103422853 A | 12/2013 |
| CN | 103543474 A | 1/2014 |
| CN | 104278989 A | 1/2015 |
| CN | 105114064 A | 12/2015 |
| CN | 105445441 A | 3/2016 |
| CN | 106093350 A | 11/2016 |
| WO | WO-2006/063711 A2 | 6/2006 |
| WO | WO-2013/180593 A1 | 12/2013 |

OTHER PUBLICATIONS

Daniel Kurtzman et al., "Dissolution vugs in fractured carbonates: A complication? Or perhaps a key for simplifying reservoir characterization", Geophysical Research Letters, vol. 34, L20409, doi: 10, 1029/2007GL031229, 2007, pp. 1-6.*

Zhao, Liangxiao et al.,"*Calculation Methods of the Oil and Gas Saturation in Complex Carbonate Reservoir*", Natural Gas Industry, vol. 25, No. 9, Sep. 30, 2015, pp. 42-44.

Zhen, Tingjiang, "*Study on Saturation Index of Heterogeneous Carbonates*", Well Logging Technology, vol. 21, No. 4, Apr. 30, 1997, pp. 254-257.

Luo Shaocheng et al., "*Research on Saturation Index $_n$ of Tight Sandstone Reservoir*", Journal of Southwest Petroleum University (Science & Technology Edition), vol. 36, No. 4, Aug. 31, 2014, pp. 116-122.

International Search Report issued for counterpart Chinese patent application No. PCT/CN2017/084304 dated Sep. 1, 2017.

First Office Action dated Dec. 4, 2017 for counterpart Chinese patent application No. 201610649337.4.

Search report dated Dec. 4, 2017 for counterpart Chinese patent application No. 201610649337.4.

Worthington, "Net Pay—What Is It? What Does It Do? How Do We Quantify It? How Do We Use It?" Oct. 2010, SPE Reservoir Evaluation & Engineering, 13(05):812-822.

* cited by examiner

METHOD AND SYSTEM FOR DETERMINING HETEROGENEOUS CARBONATE RESERVOIR SATURATION EXPONENT

CROSS-REFERENCE

This application is a U.S. national phase application of PCT/CN2017/084304, filed May 15, 2017, which claims priority to Chinese Patent Application No.: 201610649337.4, entitled "Method for Determining Heterogeneous Carbonate Reservoir Saturation Exponent", filed on Aug. 10, 2016, of which the entire contents are hereby incorporated by reference in the present application.

TECHNICAL FIELD

The present invention relates to the technical field of well logging evaluation for oil and gas reservoirs, in particular relates to a method and system for determining a saturation exponent of a heterogeneous carbonate rock reservoir.

BACKGROUND

The electrical conductivities of reservoir rocks mainly depend on the properties, saturation conditions and spatial distributions of fluids in pore spaces. For a heterogeneous carbonate rock reservoir, the pore structure has a very significant influence to electrical resistivity. Sometimes the influence of fractures and vugs to electrical resistivity is far greater than that of oil-gas saturation. Many researchers attempt to break away from the traditional method of calculating saturations purely depending on resistivity curves, which has been used for over 70 years, and try to utilize various non-electrical well logging methods to calculate the saturations of carbonate rocks, however, the application effects thereof are not good. Therefore, up to now, the saturation calculation based on electrical well logging is still the most practical and feasible method.

Archie (1942) proposed the relational expression of resistivity index-water saturation, and of formation factor-porosity for reservoirs. Li Ning (1989) provided the relational expression of resistivity index-water saturation, and of formation factor-porosity through complete mathematical derivations on the basis of a heterogeneous anisotropic stratigraphic formation model. The general relational expressions theoretically solve the problem of accurate quantitative calculation of saturation of a heterogeneous complex reservoir, however, under the current technical conditions, two critical technical problems still remain to be solved in practical application: firstly, the general relational expression is a general solution equation which can not be conveniently used in programming calculation directly, i.e., under the current technical conditions of well logging, it is quite difficult to determine all the parameters in the general relational expression, thus, in practical applications, there is a need to select the shortest form (also referred to as the optimal form) that satisfies the accuracy requirement according to actual reservoir characteristics; secondly, there is a need to select a reliable method to accurately determine each of the undetermined parameters in the optimal form, thereby enabling the finally determined calculation model to reflect the real relation between the resistivity and water saturation of the reservoir to the largest extent.

The oil-gas saturation calculation using the Archie's formulas relates to two important rock electrical parameters, i.e., cementation exponent m and saturation exponent n. How the saturation exponent n can be accurately determined has long been a key point of research for petrophysicists and well logging analysts. At present, the methods of determining the saturation exponent n can substantially be divided into two categories: one is to determine by performing rock electrical experiments and by fitting the relationship of resistivity index—water saturation; the other one is to determine by utilizing the established empirical relationships between the saturation exponent n and the reservoir parameters such as porosity and permeability. The first method belongs to a direct method and is the conventional method applied at present for determining the saturation exponent n. However, it has two deficiencies in practical applications: first, in order to determine the saturation exponent n, there is a need to conduct rock electrical experiment (such as gas-drive method) for each rock core in different saturation, but the experiment usually takes a long time; second, by using this method, it is hard to realize a dynamic determination of the value of the saturation exponent n according to the reservoir characteristics and logging data. The second method belongs to an indirect method and is the research focus at home and abroad at present. By using this method, it is easy to realize the dynamic determination of the saturation exponent n. Upon research, many researchers have also proposed methods that depend on physical parameters of the reservoir, for example, Zhu Jiajun (2010) has provided a relationship between the saturation exponent n and the porosity and formation water mineralization of sandstone reservoirs with middle or high porosity in the Shengli Oil Field, and Fu Aibin (2007) has studied the saturation exponent n by piecewise regression and correlation analysis. These studies mostly focus on sandstone reservoirs, and few of them focus on the dynamic determination method of the saturation exponent n of carbonate rocks. In addition, the existing studies are more likely to be based on analysis of the relationships between the saturation exponent n and the reservoir porosity and permeability. For heterogeneous complex carbonate rocks, the studies show that the variation range of the saturation exponent n is broad with the same porosity and permeability, therefore, how the saturation exponent n of carbonate rocks can be accurately determined is a big challenge faced in well logging evaluation at present.

SUMMARY

With respect to the above technical problem, the present invention proposes a method for determining a saturation exponent of a heterogeneous carbonate rock reservoir to enable an accurate determination thereof, thereby realizing the dynamic determination of model parameters of the saturation of the carbonate rock reservoir and improving the calculation accuracy of the oil-gas saturation.

In order to achieve the above purpose, the present application provides a method for determining a saturation exponent of a heterogeneous carbonate rock reservoir, comprising:

dividing a target rock reservoir into at least two reservoir types in accordance with a predetermined rule;

obtaining a correspondence relationship between a saturation exponent and a bound water saturation in each of the reservoir types;

determining the reservoir type of measured rock cores in accordance with the predetermined rule;

obtaining the bound water saturation of the measured rock core; and calculating the saturation exponent of the measured rock core according to the bound water saturation of the measured rock core on the basis of the correspondence relationship of the reservoir type to which the to-be-measured rock core belongs.

As a preferred embodiment, said dividing a target rock reservoir into at least two reservoir types in accordance with a predetermined rule includes:

selecting a plurality of rock core samples of the target rock reservoir; and dividing the plurality of rock core samples into at least two rock core types to represent the at least two reservoir types in accordance with the predetermined rule.

As a preferred embodiment, more than 10 rock core samples of the target reservoir are selected.

As a preferred embodiment, said selecting a plurality of rock core samples of the target reservoir includes:

determining a location and an effective thickness of the target reservoir;

determining a coring position of the target reservoir according to imaging logging data; and obtaining a plurality of rock core samples by drilling at the coring position.

As a preferred embodiment, said dividing the plurality of rock core samples into at least two rock core types to represent the at least two pore types in accordance with the predetermined rule includes:

dividing the plurality of rock core samples into two rock core types in accordance with the predetermined rule, the two rock core types including: one type is the rock core samples having developed uvgs but poor vugs connectivity; and the other type is the rock core samples containing fractures or mainly intercrystalline pores.

As a preferred embodiment, said predetermined rule includes:

if vugs can be seen but no fracture feature is present on the imaging logging data in the position corresponding to a rock core, or if a data point of the cores is located at a lower right position in a porosity-permeability cross plot, or if vugs can be seen with naked eyes but no micro-fracture is present when observing the cores, then the rock core can be classified as the cores having developed vugs but poor vug connectivity, otherwise the rock core can be classified as the core containing fractures or mainly intercrystalline pores.

As a preferred embodiment, said obtaining a correspondence relationship between a saturation exponent and a bound water saturation in each of the reservoir types includes:

obtaining the bound water saturation of each core sample;

obtaining the saturation exponent of each core sample; and linearly fitting the saturation exponent with the bound water saturation of the samples of each pore type, so as to acquire the correspondence relationship between the saturation exponent and the bound water saturation in each pore type; the correspondence relationship being as follows:

$n = aS_{wir} + b$, in which n is the saturation exponent, and $S_{wir}$ is the bound water saturation.

As a preferred embodiment, said obtaining a correspondence relationship between a saturation exponent and a bound water saturation in each pore type further includes:

selecting a number of the rock samples in each pore type according to the bound water saturation;

correspondingly, said obtaining the saturation exponent of each rock sample includes:

obtaining the saturation exponent of each core sample in a number of the rock samples in each pore type.

As a preferred embodiment, said obtaining the bound water saturation of each rock sample includes:

performing a measurement of porosity and permeability parameters and a centrifugation experiment for each core sample to determine the bound water saturation.

As a preferred embodiment, said obtaining the saturation exponent of each core sample includes:

performing a rock electrical experiment to a number of the rock core samples in each of the pore type to obtain the saturation exponent.

As a preferred embodiment, said obtaining the bound water saturation of the to-be-measured rock core includes:

conducting a measurement of porosity and permeability parameters and a centrifugation experiment for the to-be-measured rock core to determining the bound water saturation.

The present application also provides a system for determining a saturation exponent of a heterogeneous carbonate rock reservoir, comprising:

a dividing device for dividing a target rock reservoir into at least two pore types in accordance with a predetermined rule;

a first obtaining device for obtaining a correspondence relationship between a saturation exponent and a bound water saturation in each of the reservoipore types;

a determination device for determining the pore type to which a to-be-measured rock core belongs in accordance with the predetermined rule;

a second obtaining device for obtaining the bound water saturation of the to-be-measured rock core; and a calculation device for calculating the saturation exponent of the to-be-measured rock core according to the bound water saturation of the to-be-measured rock core on the basis of the correspondence relationship of the pore type to which the to-be-measured rock core belongs.

As can be seen from the above description, compared with the traditional determination method of the reservoir saturation exponent, the method proposed in the present invention has the following remarkable advantages: (1) the determination method is simple and convenient: once a relationship between the saturation exponent n and the bound water saturation $S_{wir}$ of the reservoir is established, by using this method, there is no need to perform a further rock electrical experiment of reservoir conditions for the rock cores in the target layer, i.e., the value of the reservoir saturation exponent n of other layers in the district can be determined through the bound water saturation, thereby overcoming the difficulty of complexity of the rock electrical experiment of reservoir conditions; (2) the parameters are more accurate: by using this method, the corresponding saturation exponent can be determined according to different reservoir characteristics of the target layers, thus reflecting the difference in the influences of different pore structures to the electrical properties; (3) it facilitates the dynamic determination by using well logging data: by using this method, it is possible to conveniently realize the dynamic calculation of the saturation exponent n by using the well logging data, thereby improving the calculation accuracy of the oil-gas saturation of complex carbonate reservoirs.

BRIEF DESCRIPTION OF THE DRAWINGS

In order to explain more clearly the embodiments in the present invention or the technical solutions in the prior art, the following will briefly introduce the figures needed in the description of the embodiments or the prior art. Obviously, figures in the following description are only some embodiments of the present invention, and for a person skilled in the art, other figures may also be obtained based on these figures without paying creative efforts.

DETAILED DESCRIPTION

In order to enable the persons skilled in the art to better understand the technical solutions in the present application, a clear and comprehensive description of the technical solutions in the embodiments of the present application will be made below in combination with the figures in the embodiments of the present application, and obviously, the embodiments described herein are only part of, rather than all of the embodiments of the present application. Based on the embodiments of the present application, all other embodiments obtained by ordinary skilled persons in the field without paying creative efforts should pertain to the extent of protection of the present invention.

Figure 1:
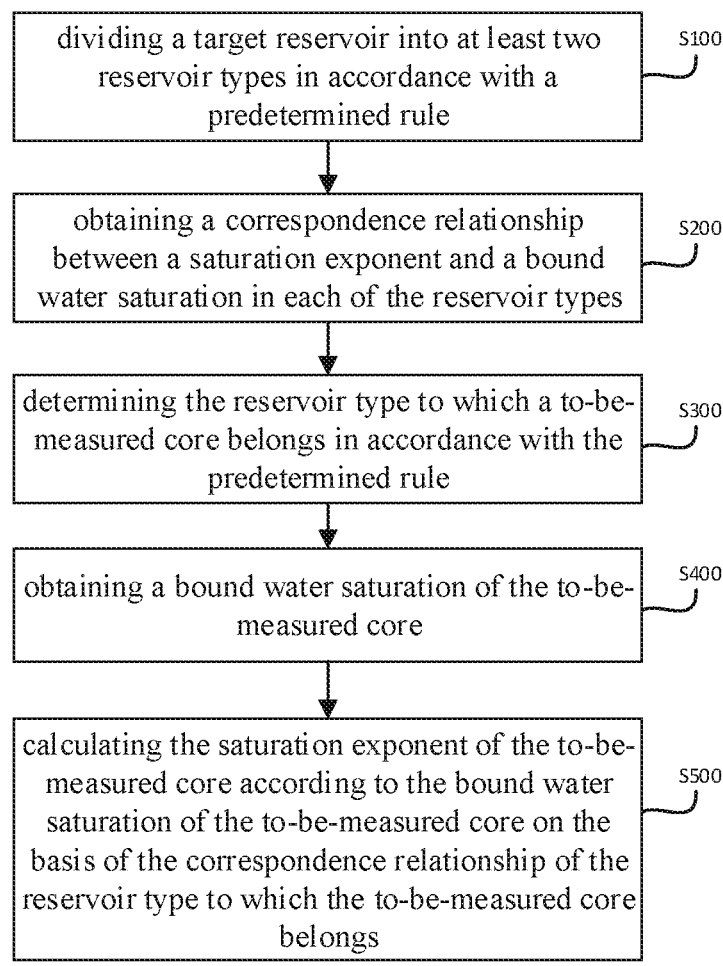
FIG. 1 is a flow chart of the method steps for determining the saturation exponent of a heterogeneous carbonate reservoir provided by an embodiment of the present application.

As shown in FIG. 1, an embodiment of the present application provides a method for determining a saturation exponent of a heterogeneous carbonate rock reservoir. The method comprises the following steps:

S100: dividing a target rock reservoir pore into at least two pore types in accordance with a predetermined rule;

this step divides the target rock reservoir pore into at least two pore types in consideration of the features of the pore structure of the heterogeneous carbonate rock reservoir; the pore structures of different reservoir types have differences from each other.

In one embodiment, said dividing a target rock reservoir pore into at least two pore types in accordance with a predetermined rule (step S100) includes the following sub-steps:

S110: selecting a plurality of rock samples of the target rock reservoir;

in order to better reflect the reservoir pore types, in this step, it is preferred to select more than 10 rock core samples of the target rock reservoir.

In the step S110, representative rock samples of the studied region can be selected, which means that a location and an effective thickness of the target layer are determined based on a comprehensive analysis of data such as conventional and imaging well logging, and the representative rock core samples are obtained by drilling after a coring position is determined according to the variation characteristics of the data such as conventional and imaging well logging in a longitudinal direction.

To be specific, said selecting a plurality of core samples of the target rock reservoir (step S110) may include the following sub-steps: S111: determining a location and an effective thickness of the target rock reservoir; S112: determining a coring position of the target rock reservoir according to imaging logging data; S113: obtaining a plurality of rock core samples by drilling at the coring position.

S120: dividing the plurality of rock core samples into at least two pore types to represent the at least two pore types in accordance with the predetermined rule;

in this step, the pore features of the reservoir where the rock core samples are located are represented by the pore features of the core samples, which is also the purpose of selecting more than 10 samples in the previous step, as such the features of the rock reservoir where the rock core samples are located are represented more subtly and accurately by the core samples.

Preferably, said dividing the plurality of rock core samples into at least two pore types to represent the at least two reservoir types in accordance with the predetermined rule (step S120) may include: S121: dividing the plurality of core samples into two pore types in accordance with the predetermined rule; the two pore types include: one type is the rock core samples having developed vugs but poor vug connectivity (the first type); the other type is the rock core samples containing fractures or mainly intercrystalline pores (the second type).

The predetermined rule may include: if vugs can be seen but no fracture feature is present on the imaging logging data corresponding to a core, or if a data point of the core is located at a lower right position in a porosity permeability cross plot (porosity-permeability cross plot), or if vugs can be seen with naked eyes but no micro-fracture is present when observing the core, then the core can be classified as the core having developed vugs but poor pore connectivity, otherwise the rock core can be classified as the core containing fractures or mainly intercrystalline pores.

S200: obtaining a correspondence relationship between a saturation exponent and a bound water saturation in each of the reservoir types;

wherein, the step S200 can be carried out through the following steps: S210: obtaining the bound water saturation of each of the core samples; S220: obtaining the saturation exponent of each of the core samples; S230: linearly fitting the saturation exponent with the bound water saturation of the rock samples of each of the reservoir types, so as to acquire the correspondence relationship between the saturation exponent and the bound water saturation in each of the reservoir types. The correspondence relationship is: $n=aS_{wir}+b$, wherein, n is the saturation exponent, and $S_{wir}$ is the bound water saturation.

In the step S200, first, a measurement of porosity and permeability parameters is performed for the selected core samples, and then a centrifugation experiment is performed for the selected cores. Reference should be made to properties of the pores and pressures of the reservoir for the choice of a centrifugal force in the experiment. In the centrifugation experiment, a water-saturated weight of the core sample should be measured first, then the centrifugation experiment is performed under a certain rotational speed (or centrifugal force), after the experiment is finished, a weight of the core sample after the centrifugation is measured, and the bound water saturation of the rock core is calculated. Namely, said obtaining the bound water saturation of each of the core samples (step S210) may include: performing a measurement of porosity and permeability parameters and a centrifugation experiment for each of the core samples to determine the bound water saturation.

In the experiment, the type and salinity of the formation water are determined depending on data of analyses of the formation water in the studied region, and the experimental temperature and confining pressure are determined depending on the temperature and pressure of the reservoir of the target layer. On the basis of the rock electrical experiment with displacement, a diagram of relationship between the resistivity index and the water saturation of the core sample is drawn, and the value of the saturation exponent n of each core is determined using the Archie's formulas. Namely, said obtaining the saturation exponent of each of the core samples (step S220) may include: performing a rock electrical experiment to a number of the rock core samples in each of the reservoir types to obtain the saturation exponent.

Further, in order to obtain a reasonable and accurate calculation result, said obtaining a correspondence relationship between a saturation exponent and a bound water saturation in each of the reservoir types (step S200) may also include the following step: S225: selecting a number of the core samples in each of the reservoir types according to the bound water saturation.

Correspondingly, the step S230 of obtaining the saturation exponent of each of the core samples includes (is): S231: obtaining the saturation exponent of each of the core samples in a number of the core samples in each of the reservoir types.

By the step S225, it is possible to eliminate unreasonable data, i.e., the bound water saturations which obviously do not conform to the type of the reservoir where the core sample is located, and thereby the calculation accuracy is improved. Researches show that the bound water saturations of the first type of rock cores are usually low, and the bound water saturations of the second type of rock cores are usually high. In each type of rock cores, representative cores are selected according to the value of the bound water saturation to carry out the rock electrical experiment. For example, if, in the studied region, the maximum bound water saturation of the first type of cores is 50%, then there is a need to select the representative rock cores with a bound water saturation of 0-50% from the first type of rock cores to perform the rock electrical experiment, and data above 50% can be eliminated. After the unreasonable core samples are eliminated, the rock electrical experiment is performed for each of the rest core samples (i.e., the step S231).

In the step S230, the relationships between the saturation exponent n and the bound water saturation $S_{wir}$ of different reservoir types in the district is determined by fitting according to the calculation results of the bound water saturation $S_{wir}$ and the saturation exponent n of the representative cores selected.

The first type: the correspondence relationship between the saturation exponent and the bound water saturation of the reservoir having developed vugs but poor pore connectivity is:

$$n=a_1S_{wir}+b \quad (1)$$

The second type: the correspondence relationship between the saturation exponent and the bound water saturation of the reservoir containing fractures or mainly intercrystalline pores is:

$$n=a_2S_{wir}+b_2 \quad (2)$$

The parameters $a_1$, $b_1$ and $a_2$, $b_2$ in the formulas are constants for specific reservoir in some district, but the values of the parameters in different reservoir and different districts have differences from each other, hence the values of $a_1$, $b_1$ and $a_2$, $b_2$ can be determined by means of core experiments.

S300: determining the reservoir type to which a to-be-measured rock core belongs in accordance with the predetermined rule;

in this step, S300 can determine the reservoir type to which the to-be-measured core belongs by means of the above mentioned predetermined rule, and the rock electrical experiment has not yet been conducted for the to-be-measured core.

The predetermined rule may include: if vugs can be seen but no fracture feature is present on the imaging logging data corresponding to a core, or if a data point of the core is located at a lower right position in a porosity permeability cross plot, or if vugs can be seen with naked eyes but no micro-fracture is present when observing the rock core, the core can be classified as the core having developed vugs but poor pore connectivity, otherwise the rock core can be classified as the core containing fractures or mainly intercrystalline pores.

S400: obtaining a bound water saturation of the to-be-measured rock core;

in this step, the porosity and permeability parameters of the to-be-measured core are measured, and a centrifugation experiment is performed to the to-be-measured core. Reference should be made to the properties of the pores and pressure of the reservoir for the choice of the centrifugal force in the experiment. In the centrifugation experiment, a water-saturated weight of the to-be-measured rock core should be measured first, then the centrifugation experiment is performed under a certain rotational speed (or centrifugal force), after the experiment is finished, a weight of the to-be-measured rock core after the centrifugation is measured, and the bound water saturation of the to-be-tested core is calculated.

S500: calculating the saturation exponent of the to-be-measured core according to the bound water saturation of the to-be-measured core on the basis of the correspondence relationship of the reservoir type to which the to-be-measured core belongs.

For example, by the step S300 it is determined that the reservoir type to which the to-be-measured core belongs to the first type, and by the step S400 it is determined that the bound water saturation of the to-be-measured rock core is $S_{wir\ to-be-measured}$, then, in the step S500, the $S_{wir\ to-be-measured}$ is substituted in the correspondence relationship between the saturation exponent and the bound water saturation in the first type of reservoirs in the step S230, and thereby the saturation exponent of the to-be-measured rock core is obtained: $n_{to-be-measured}=a_1S_{wir\ to-be-measured}+b_1$.

As can be seen from the above description, compared with the traditional determination method of the reservoir saturation exponent, the method proposed in the present invention has the following remarkable advantages: (1) the determination method is simple and convenient: once a relationship between the saturation exponent n and the bound water saturation $S_{wir}$ of the district is established, by using this method, there is no need to perform a further rock electrical experiment of reservoir conditions for the rock cores in the target reservoir, i.e., the values of the reservoir saturation exponent n of other layers in the district can be determined through the bound water saturation, thereby overcoming the difficulty of complexity of the rock electrical experiment of reservoir conditions; (2) the parameters are more accurate: by using this method, the corresponding saturation exponents can be determined according to different reservoir characteristics of the target layers, thus reflecting the difference in the influences of different pore structures to the electrical properties; (3) it facilitates the dynamic determination by using well logging data: by using this method, it is possible to conveniently realize the dynamic calculation of the saturation exponent n by using the well logging data, thereby improving the calculation accuracy of the oil-gas saturation of complex carbonate rocks.

Further detailed description of the specific embodiments of the present invention will be given below with reference to the accompanying drawings.

On the basis of the comprehensive analyses of conventional and imaging logging data of a certain reservoir of the Changqing Oil Field, the location and effective thickness of the target layer have been determined, and according to the variation characteristics of the conventional and imaging logging data in a longitudinal direction, the coring position is determined and 19 pieces of representative plug-size cores (which are the rock core samples) are obtained by drilling.

First, a measurement of porosity and permeability parameters is performed for the selected 19 pieces of plug-size cores, and after that, a centrifugation experiment is performed to the selected cores. In the centrifugation experiment, at first a water-saturated weight of each core is measured, and then a centrifugation experiment is performed under a rotational speed of 3000 rps, and after the experiment is finished, the weight of each core after the centrifugation is measured.

According to imaging logging data, the porosity and permeability features and the rock core observations at the depth corresponding to the selected cores, the mentioned 19 cores are respectively divided into two types with different pore structures: one type is the cores, 10 pieces in total, having developed vugs but poor pore connectivity, and the other type is the cores, 9 pieces in total, containing fractures of mainly intercrystalline pores. The specific classification method according to the pore structures of the rock cores is that: if vugs can be seen but no fracture feature is present on the imaging logging data corresponding to a core, or if a data point of the rock core is located at a lower right position in a porosity permeability cross plot, or if vugs can be seen with naked eyes but no micro-fracture is present when observing the core, then the core can be classified as the core having developed vugs but poor pore connectivity, otherwise the core can be classified as the second type, i.e., the core containing fractures or mainly intercrystalline pores. If a three-dimensional CT test is conducted for the rock cores, it would be more convenient and accurate to divide the cores into the cores having developed vugs but poor pore connectivity and the cores containing fractures or mainly intercrystalline pores, according to the CT data.

As regards the above mentioned two types of cores with different pore structures, representative cores are selected according to the bound water saturation so as to carry out a displacement rock electrical experiment of reservoir conditions and calculate the saturation exponent n of the rock cores. According to the bound water saturation, 7 pieces of the first type of cores (i.e., the cores having developed vugs but poor pore connectivity) and 5 pieces of the second type of cores (i.e., the cores containing fractures or mainly intercrystalline pores) from a certain layer in the Changqing Oil Field are selected to carry out a semi-permeable plate gas-drive rock electrical experiment of reservoir conditions. In the experiment, the salinity is 100000 ppm, the water type is NaCl type, and the resistivity of formation water Rw is 0.032 $\Omega \cdot m$. According to the reservoir depth of the target region, the confining pressure in the experiment is 15 Mpa.

According to the resistivities of the cores under different water saturations obtained in the experiment, a diagram of the relationship between the resistivity index and the water saturation of each rock core piece is drawn, and the value of the saturation exponent n thereof is determined using the Archie's formulas.

According to the calculation results of the bound water saturation $S_{wir}$ and the saturation exponent n of the representative cores selected, the relationship between the saturation exponent n and the bound water saturation $S_{wir}$ of different reservoir types of the district is determined by fitting.

Figure 2:
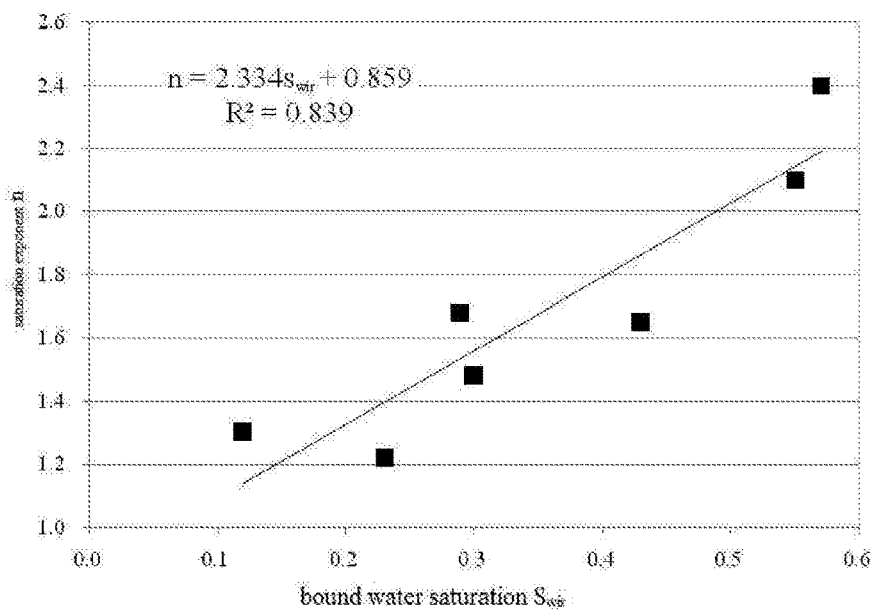
FIG. 2 is a diagram of the correspondence relationship between the saturation exponent n and the bound water saturation $S_{wir}$ of reservoirs having developed vugs but poor vug connectivity in the Changqing Oil Field.

The diagram of the relationship between the bound water saturation $S_{wir}$ and the saturation exponent n of the first type of reservoir, i.e., the reservoir having developed vugs but poor pore connectivity, of a certain layer of the Changqing Oil Field is shown in FIG. 2, and the relational expression of quantitative fitting is:

$$n = 2.342 S_{wir} + 0.857 \qquad (1)$$

Figure 3:
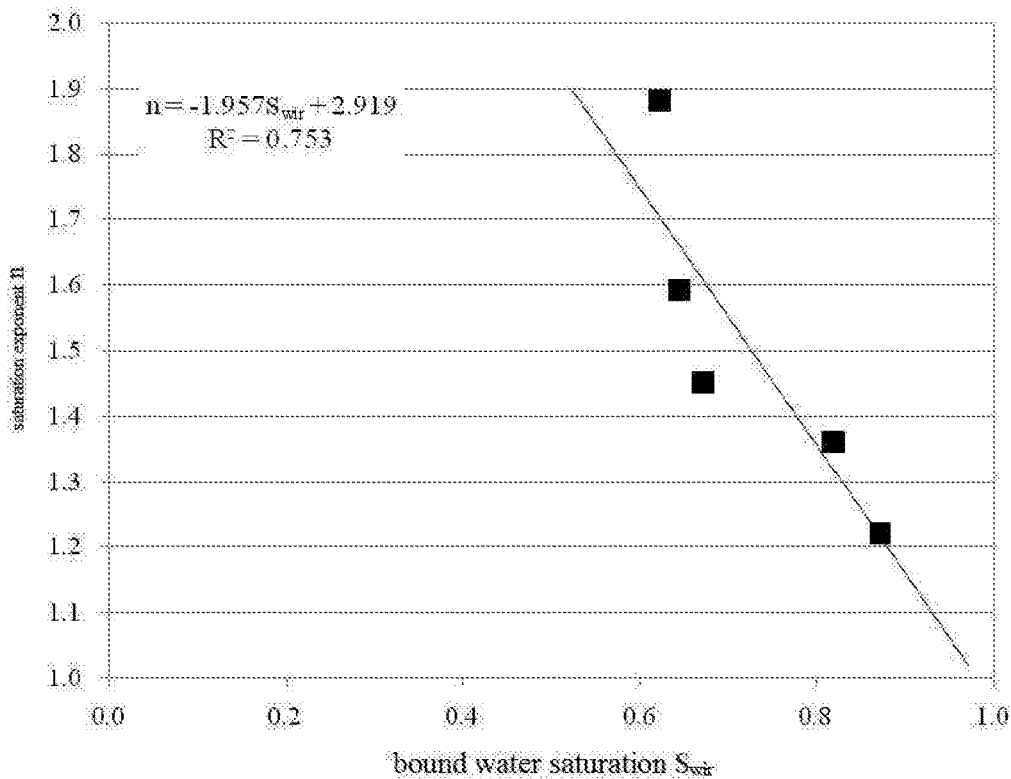
FIG. 3 is a diagram of the correspondence relationship between the saturation exponent n and the bound water saturation $S_{wir}$ of reservoirs containing fractures or mainly intercrystalline pores in the Changqing Oil Field.

The diagram of the relationship between the bound water saturation $S_{wir}$ and the saturation exponent n of the second type of reservoir, i.e., the reservoir containing fractures or mainly intercrystalline pores, of a certain layer of the Changqing Oil Field is shown in FIG. 3, and the relational expression of quantitative fitting is:

$$n = -1.057 S_{wir} + 2.919 \qquad (2)$$

As for the cores A and B (which are the to-be-measured rock cores) of a certain layer of the Changqing Oil Field which have not gone through the rock electrical experiment, first, the type of the pore structures of the two rock cores is analyzed, and according to the above mentioned analyzing method (predetermined rule), the core A is determined as pertaining to the first type, and the core B to the second type; according to the centrifugation result, the bound water saturation $S_{wir}$ of core A is calculated to be 0.38, and the bound water saturation $S_{wir}$ of core B is calculated to be 0.71; and by using the previously established relationship between the bound water saturation $S_{wir}$ and the saturation index exponent n of the two types of reservoir cores, it is possible to obtain rapidly and accurately by calculation that the saturation exponent of the rock core A is 1.75, and the saturation exponent of the core B is 1.53. Similarly, the above method can be utilized to determine the saturation exponent of other cores in the corresponding layer.

Another embodiment of the present application also provides a system for determining a saturation exponent of a heterogeneous carbonate rock reservoir. The system comprises: a dividing device for dividing a target rock reservoir into at least two reservoir types according to a predetermined rule; a first obtaining device for obtaining a correspondence relationship between a saturation exponent and a bound water saturation in each of the rock reservoir types; a determination device for determining the reservoir type to which a to-be-measured rock core belongs according to the predetermined rule; a second obtaining device for obtaining the bound water saturation of the to-be-measured core; and a calculation device for calculating the saturation exponent of the to-be-measured core according to the bound water saturation of the to-be-measured core on the basis of the correspondence relationship of the reservoir type to which the to-be-measured core belongs.

The system for determining a saturation exponent of a heterogeneous carbonate rock reservoir in this embodiment is in correspondence with the method for determining a saturation exponent of a heterogeneous carbonate rock reservoir of the present invention. It can realize the embodiment in the method for determining a saturation exponent of a heterogeneous carbonate rock reservoir of the present application and achieve the technical effect thereof. Therefore, the present application will not provide redundant descriptions for detail here.

The above has shown and described the basis principle, main features and advantages of the present invention. It shall be appreciated by those skilled in the art that, the present invention is not limited by the above embodiments, the above embodiments and what is described in the Description only illustrate the principles of the present invention. Without departing from the spirit of the present invention, there are different variations and improvements for the present invention, which should all be included in the protection scope of the present invention. The protection scope of the present invention is defined by the attached claims and the equivalents thereof.

The invention claimed is:

1. A method for determining a saturation exponent of a heterogeneous carbonate rock reservoir, comprising:
dividing a target reservoir into at least two reservoir types in accordance with a predetermined rule, which includes
selecting a plurality of core samples of the target rock reservoir; and
dividing the plurality of core samples into at least two core types to represent the at least two reservoir types in accordance with the predetermined rule;
obtaining a correspondence relationship between a saturation exponent and a bound water saturation in each of the reservoir types, which includes
obtaining the bound water saturation of each of the core samples;
obtaining the saturation exponent of each of the core samples, which includes performing a rock electrical experiment to a number of the rock core samples in each of the reservoir types to acquire the saturation exponent; and
linearly fitting the saturation exponent with the bound water saturation of the core samples that have gone through the rock electrical experiment in each of the reservoir types, so as to acquire the correspondence relationship between the saturation exponent and the bound water saturation in each of the reservoir types;
the correspondence relationship being as follows $n = aS_{wir} + b,$ in which n is the saturation exponent, and $S_{wir}$ is the bound water saturation;
determining the reservoir type to which a to-be-measured core belongs in accordance with the predetermined rule, wherein the to-be-measured core is the core sample that has not gone through the rock electrical experiment;
obtaining a bound water saturation of the to-be-measured core; and
calculating the saturation exponent of the to-be-measured core according to the bound water saturation of the to-be-measured core on the basis of the correspondence relationship of the reservoir type to which the to-be-measured core belongs.

2. The method according to claim 1, wherein, 19 pieces of core samples of the target reservoir are selected.

3. The method according to claim 1, wherein, said selecting a plurality of core samples of the target reservoir includes:
determining a location and an net pay thickness of the target reservoir;
determining a coring position of the target reservoir according to imaging logging data; and
obtaining a plurality of core samples by drilling at the coring position.

4. The method according to claim 1, wherein, said dividing the plurality of core samples into at least two types to represent the at least two reservoir types in accordance with the predetermined rule includes:
dividing the plurality of core samples into two types in accordance with the predetermined rule, the two core types including: one type is core samples having developed vugs but poor pore connectivity; the other type is core samples containing fractures or mainly intercrystalline pores.

5. The method according to claim 4, wherein, the predetermined rule includes:
if vugs can be seen but no fracture feature is present on the imaging logging data corresponding to a core, or if vugs can be seen with naked eyes but no micro-fracture is present when observing the core, then the core can be classified as the core having developed vugs but poor pore connectivity, otherwise the core can be classified as the core containing fractures or mainly intercrystalline pores.

6. The method according to claim 1, wherein, said obtaining a correspondence relationship between a saturation exponent and a bound water saturation in each of the reservoir types further includes:
selecting a number of the core samples in each of the reservoir types according to the bound water saturation;
correspondingly, said obtaining the saturation exponent of each of the core samples includes:
obtaining the saturation exponent of each of the core samples in a number of the core samples in each of the reservoir types.

7. The method according to claim 1, wherein, said obtaining the bound water saturation of each of the core samples includes:
performing a measurement of porosity and permeability parameters and a centrifugation experiment for each of the core samples to determine the bound water saturation.

8. The method according to claim 1, wherein, said obtaining the bound water saturation of the to-be-measured core includes:
performing a measurement of porosity and permeability parameters and a centrifugation experiment for the to-be-measured core to determining the bound water saturation.

* * * * *